US012285175B2

(12) United States Patent
Griffin (10) Patent No.: US 12,285,175 B2
(45) Date of Patent: *Apr. 29, 2025

(54) OCCLUSION DEVICE (71) Applicant: Cerus Endovascular Limited, Oxford (GB)

(72) Inventor: Stephen Griffin, Fremont, CA (US)

(73) Assignee: Stryker Ireland Technology Ltd., Carrigtwohill (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,106

(22) Filed: Apr. 3, 2023

(65) Prior Publication Data
US 2023/0240687 A1 Aug. 3, 2023

Related U.S. Application Data (63) Continuation of application No. 16/952,756, filed on Nov. 19, 2020, now Pat. No. 11,648,013, which is a
(Continued)

(51) Int. Cl.
*A61B 17/12* (2006.01)
*A61B 90/00* (2016.01)
*A61B 17/00* (2006.01)

(52) U.S. Cl.
CPC .. *A61B 17/12122* (2013.01); *A61B 17/12172* (2013.01); *A61B 17/12177* (2013.01);
(Continued)

(58) Field of Classification Search
CPC ........ A61B 17/12122; A61B 17/12113; A61B 17/12145; A61B 17/12031; A61B 17/12172; A61B 17/12177; A61B 90/39
See application file for complete search history.

(56) References Cited

U.S. PATENT DOCUMENTS 2,849,002 A 8/1958 Oddo
3,480,017 A 11/1969 Shute
(Continued)

FOREIGN PATENT DOCUMENTS

CA 2779483 5/2011
CA 2946078 11/2015
(Continued)

OTHER PUBLICATIONS

US 9,034,010 B2, 05/2015, Amin (withdrawn)
(Continued)

*Primary Examiner* — Tuan V Nguyen
(74) *Attorney, Agent, or Firm* — McDonnell Boehnen Hulbert & Berghoff LLP (57) ABSTRACT

Provided herein is an occlusion device comprising: (a) a substantially solid marker band having an inner and outer diameter, a proximal end, and a distal end; and (b) a resilient mesh body attached within the marker band, wherein the body is a length y, and wherein the body comprises a bolus of additional resilient mesh material of a length x, wherein y is greater than x, and wherein the body extends distally from the marker band having a first delivery shape and a second expandable deployed shape. Also provided herein is a kit comprising the occlusion device disclosed herein and a means for delivery thereof. Methods of manufacture and use of the occlusion device disclosed herein are also disclosed.

20 Claims, 2 Drawing Sheets

Related U.S. Application Data continuation of application No. 16/080,626, filed as application No. PCT/EP2017/055765 on Mar. 13, 2017, now Pat. No. 10,869,672.

(60) Provisional application No. 62/307,137, filed on Mar. 11, 2016.

(52) U.S. Cl.
CPC .... *A61B 90/39* (2016.02); *A61B 2017/00243* (2013.01); *A61B 2017/00575* (2013.01); *A61B 2090/3966* (2016.02)

(56) References Cited

U.S. PATENT DOCUMENTS

| | | |
|---|---|---|
| 4,364,392 A | 12/1982 | Strother et al. |
| 4,395,806 A | 8/1983 | Wonder et al. |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,423,829 A | 6/1995 | Pham et al. |
| 5,496,277 A | 3/1996 | Temlin et al. |
| 5,624,449 A | 4/1997 | Pham et al. |
| 5,733,294 A | 3/1998 | Forber et al. |
| 5,891,128 A | 4/1999 | Gia et al. |
| 5,928,260 A | 7/1999 | Chin et al. |
| 6,007,573 A | 12/1999 | Wallace et al. |
| 6,024,756 A | 2/2000 | Pham |
| 6,080,191 A | 6/2000 | Thaler |
| 6,096,021 A | 8/2000 | Helm et al. |
| 6,113,609 A | 9/2000 | Adams |
| 6,123,714 A | 9/2000 | Gia et al. |
| 6,152,144 A | 11/2000 | Lesh et al. |
| 6,168,579 B1 | 1/2001 | Tsugita |
| 6,168,622 B1 | 1/2001 | Mazzocclli |
| 6,221,086 B1 | 4/2001 | Forber |
| 6,270,515 B1 | 8/2001 | Linden et al. |
| 6,315,787 B1 | 11/2001 | Tsugita et al. |
| 6,334,048 B1 | 12/2001 | Edvardsson et al. |
| 6,419,686 B1 | 7/2002 | McLeod et al. |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Tassel et al. |
| 6,569,190 B2 | 5/2003 | Whalen, II et al. |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,663,068 B2 | 12/2003 | Huang |
| 6,669,719 B2 | 12/2003 | Wallace et al. |
| 6,669,721 B1 | 12/2003 | Bose et al. |
| 6,689,159 B2 | 2/2004 | Lau et al. |
| 6,780,196 B2 | 8/2004 | Chin et al. |
| 6,811,560 B2 | 11/2004 | Jones |
| 6,833,003 B2 | 12/2004 | Jones et al. |
| 6,855,154 B2 | 2/2005 | Abdel-Gawwad |
| 6,949,116 B2 | 9/2005 | Solymar et al. |
| 6,953,472 B2 | 10/2005 | Palmer |
| 7,044,134 B2 | 5/2006 | Khairkhahan et al. |
| 7,093,527 B2 | 8/2006 | Rapaport et al. |
| 7,128,073 B1 | 10/2006 | Burg et al. |
| 7,128,736 B1 | 10/2006 | Abrams et al. |
| 7,152,605 B2 | 12/2006 | Khairkhahan et al. |
| 7,195,636 B2 | 3/2007 | Avellanet et al. |
| 7,229,454 B2 | 6/2007 | Tran et al. |
| 7,229,461 B2 | 6/2007 | Chin et al. |
| 7,232,461 B2 | 6/2007 | Ramer |
| 7,306,622 B2 | 12/2007 | Jones |
| 7,371,249 B2 | 5/2008 | Douk et al. |
| 7,410,482 B2 | 8/2008 | Murphy et al. |
| 7,572,288 B2 | 8/2009 | Cox |
| 7,597,704 B2 | 10/2009 | Frazier et al. |
| 7,695,488 B2 | 4/2010 | Berenstein et al. |
| 7,713,264 B2 | 5/2010 | Murphy |
| 7,722,641 B2 | 5/2010 | Burg et al. |
| 7,744,652 B2 | 6/2010 | Morsi |
| 7,828,818 B2 | 11/2010 | Zhang et al. |
| 7,892,254 B2 | 2/2011 | Klint |
| 8,034,061 B2 | 10/2011 | Amplatz et al. |
| 8,066,757 B2 | 11/2011 | Ferrera |
| 8,075,585 B2 | 12/2011 | Lee et al. |
| 8,080,032 B2 | 12/2011 | Burg et al. |
| 8,088,140 B2 | 1/2012 | Ferrera |
| 8,142,456 B2 | 3/2012 | Rosqueta et al. |
| 8,221,483 B2 | 7/2012 | Ford et al. |
| 8,252,040 B2 | 8/2012 | Cox |
| 8,261,648 B1 | 9/2012 | Marchand et al. |
| 8,262,692 B2 | 9/2012 | Rudakov |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand et al. |
| 8,454,633 B2 | 6/2013 | Amolatz et al. |
| 8,470,013 B2 | 6/2013 | Duggal et al. |
| 8,500,751 B2 | 8/2013 | Rudakov et al. |
| 8,523,897 B2 | 9/2013 | van der Burg et al. |
| 8,535,343 B2 | 9/2013 | Burg et al. |
| 8,454,514 B2 | 10/2013 | Ferrera |
| 8,562,667 B2 | 10/2013 | Cox |
| 8,574,262 B2 | 11/2013 | Ferrera |
| 8,585,713 B2 | 11/2013 | Ferrera |
| 8,597,320 B2 | 12/2013 | Sepetka |
| 8,663,273 B2 | 3/2014 | Khairkhahan |
| 8,696,701 B2 | 4/2014 | Becking |
| 8,715,312 B2 | 5/2014 | Burke |
| 8,715,316 B1 | 5/2014 | Janardhan et al. |
| 8,747,453 B2 | 6/2014 | Amplatz |
| 8,771,294 B2 | 7/2014 | Sepetka |
| 8,834,519 B2 | 9/2014 | Vanderburg |
| 8,926,680 B2 | 1/2015 | Ferrera |
| 8,945,172 B2 | 2/2015 | Ferrera |
| 9,034,054 B2 | 5/2015 | Gerberding |
| 9,039,724 B2 | 5/2015 | Amplatz et al. |
| 9,060,077 B2 | 6/2015 | Sayama |
| 9,078,658 B2 | 7/2015 | Hewitt |
| 9,107,670 B2 | 8/2015 | Hannes |
| 9,138,213 B2 | 9/2015 | Amin |
| 9,161,758 B2 | 10/2015 | Figulla |
| 9,168,043 B2 | 10/2015 | Vanderburg |
| 9,179,918 B2 | 11/2015 | Levy |
| 9,186,487 B2 | 11/2015 | Dumbl et al. |
| 9,198,668 B2 | 12/2015 | Theobald |
| 9,198,670 B2 | 12/2015 | Hewitt |
| 9,198,687 B2 | 12/2015 | Fulkerson |
| 9,220,522 B2 | 12/2015 | Fulkerson |
| 9,259,337 B2 | 2/2016 | Cox |
| 9,271,736 B2 | 3/2016 | Heipl |
| 9,295,473 B2 | 3/2016 | Hewitt |
| 9,307,998 B2 | 4/2016 | Chin |
| 9,314,326 B2 | 4/2016 | Wallace |
| 9,387,098 B2 | 7/2016 | Ferrera |
| 9,474,517 B2 | 10/2016 | Amin |
| 9,492,174 B2 | 11/2016 | Hewitt |
| 9,498,604 B2 | 11/2016 | Dubrul |
| 9,532,772 B2 | 1/2017 | Moszner |
| 9,539,122 B2 | 1/2017 | Burke |
| 9,545,300 B2 | 1/2017 | Cully |
| 9,572,698 B2 | 2/2017 | Franano |
| 9,597,087 B2 | 3/2017 | Marchand |
| 9,622,770 B2 | 4/2017 | Trapp |
| 9,629,635 B2 | 4/2017 | Hewitt |
| 9,795,400 B2 | 10/2017 | Davidson |

(56) References Cited

U.S. PATENT DOCUMENTS

| | | |
|---|---|---|
| 9,826,980 B2 | 11/2017 | Figulla |
| 9,839,430 B2 | 12/2017 | Willems |
| 9,861,467 B2 | 1/2018 | Cully |
| 9,877,726 B2 | 1/2018 | Liu |
| 9,918,720 B2 | 3/2018 | Marchand |
| 9,943,299 B2 | 4/2018 | Khairkhahan |
| 9,955,976 B2 | 5/2018 | Hewitt |
| 9,962,146 B2 | 5/2018 | Hebert |
| 9,980,733 B2 | 5/2018 | Badruddin |
| 10,028,745 B2 | 7/2018 | Morsi |
| 10,028,747 B2 | 7/2018 | Connor |
| 10,076,399 B2 | 9/2018 | Davidson |
| 10,123,803 B2 | 11/2018 | Ferrera et al. |
| 10,130,372 B2 | 11/2018 | Griffin |
| 10,136,896 B2 | 11/2018 | Hewitt et al. |
| 10,159,490 B2 | 12/2018 | Wallace et al. |
| 10,231,722 B2 | 3/2019 | Hebert et al. |
| 10,238,393 B2 | 3/2019 | Marchand et al. |
| 10,265,075 B2 | 4/2019 | Porter et al. |
| 10,278,705 B2 | 5/2019 | Amin et al. |
| 10,285,678 B2 | 5/2019 | Hebert et al. |
| 10,285,679 B2 | 5/2019 | Hebert et al. |
| 10,285,711 B2 | 5/2019 | Griffin |
| 10,299,775 B2 | 5/2019 | Hebert et al. |
| 10,342,546 B2 | 7/2019 | Sepetka et al. |
| 10,383,635 B2 | 8/2019 | Wallace et al. |
| 10,398,441 B2 | 9/2019 | Warner et al. |
| 10,398,444 B2 | 9/2019 | Morsi |
| 10,433,851 B2 | 10/2019 | Adams et al. |
| 10,478,194 B2 | 11/2019 | Rhee et al. |
| 10,499,939 B2 | 12/2019 | Davidson |
| 10,537,451 B2 | 1/2020 | Franano et al. |
| 10,543,015 B2 | 1/2020 | Walzman |
| 10,543,115 B2 | 1/2020 | Franano et al. |
| 10,548,607 B2 | 2/2020 | Walzman |
| 10,561,411 B1 | 2/2020 | Cole et al. |
| 10,561,441 B2 | 2/2020 | Walzman |
| 10,603,070 B2 | 3/2020 | Walzman |
| 10,610,231 B2 | 4/2020 | Marchand et al. |
| 10,617,428 B2 | 4/2020 | Walzman |
| 10,653,403 B2 | 5/2020 | Hebert et al. |
| 10,716,549 B2 | 7/2020 | Keillor |
| 10,716,573 B2 | 7/2020 | Connor |
| 10,716,574 B2 | 7/2020 | Lorenzo et al. |
| 10,729,447 B2 | 8/2020 | Shimizu et al. |
| 10,743,852 B2 | 8/2020 | Moszner et al. |
| 10,743,884 B2 | 8/2020 | Lorenzo |
| 10,751,065 B2 | 8/2020 | Soto Del Valle et al. |
| 10,751,066 B2 | 8/2020 | Lorenzo |
| 10,772,747 B2 | 9/2020 | Fischer et al. |
| 10,808,341 B2 | 10/2020 | Koppe |
| 10,813,645 B2 | 10/2020 | Hewitt et al. |
| 10,835,257 B2 | 11/2020 | Ferrera et al. |
| 10,856,879 B2 | 12/2020 | Badruddin et al. |
| 10,856,880 B1 | 12/2020 | Badruddin et al. |
| 10,869,672 B2 | 12/2020 | Griffin |
| 10,881,413 B2 | 1/2021 | Merrit et al. |
| 10,888,333 B2 | 1/2021 | Kealey et al. |
| 10,905,430 B2 | 2/2021 | Lorenzo et al. |
| 10,925,612 B2 | 2/2021 | Wallace et al. |
| 10,939,914 B2 | 3/2021 | Hewitt et al. |
| 10,939,915 B2 | 3/2021 | Gorochow et al. |
| 10,952,739 B2 | 3/2021 | Plaza et al. |
| 10,959,735 B2 | 3/2021 | Morsi |
| 10,980,545 B2 | 4/2021 | Bowman et al. |
| 11,006,940 B2 | 5/2021 | Herbert et al. |
| 11,033,277 B2 | 6/2021 | Wolfe et al. |
| 11,045,177 B2 | 6/2021 | Walzman |
| 11,045,203 B2 | 6/2021 | Sepetka et al. |
| 11,058,430 B2 | 7/2021 | Gorochow et al. |
| 11,058,431 B2 | 7/2021 | Pereira et al. |
| 11,076,860 B2 | 8/2021 | Lorenzo |
| 11,076,861 B2 | 8/2021 | Gorochow et al. |
| 11,090,078 B2 | 8/2021 | Walzman |
| 11,090,176 B2 | 8/2021 | Franano et al. |
| 11,123,077 B2 | 9/2021 | Lorenzo et al. |
| 11,134,933 B2 | 10/2021 | Amplatz et al. |
| 11,154,302 B2 | 10/2021 | Lorenzo |
| 11,166,731 B2 | 11/2021 | Wolfe et al. |
| 11,179,159 B2 | 11/2021 | Cox et al. |
| 11,185,335 B2 | 11/2021 | Badruddin et al. |
| 11,202,636 B2 | 12/2021 | Zaidat et al. |
| 11,241,223 B2 | 2/2022 | Herbert et al. |
| 11,253,261 B2 | 2/2022 | Jayaraman |
| 11,266,414 B2 | 3/2022 | Fulton, III |
| 11,284,901 B2 | 3/2022 | Griffin |
| 2001/0041900 A1 | 11/2001 | Callister |
| 2002/0082638 A1 | 6/2002 | Porter et al. |
| 2002/0143349 A1 | 10/2002 | Gifford, II et al. |
| 2002/0169473 A1 | 11/2002 | Sepetka |
| 2002/0188314 A1 | 12/2002 | Anderson et al. |
| 2003/0055451 A1 | 3/2003 | Jones et al. |
| 2003/0120337 A1 | 6/2003 | Tassel et al. |
| 2003/0171739 A1 | 9/2003 | Murphy et al. |
| 2003/0176884 A1 | 9/2003 | Berrada |
| 2003/0181927 A1 | 9/2003 | Wallace |
| 2003/0195553 A1 | 10/2003 | Wallace et al. |
| 2003/0220667 A1 | 11/2003 | Van Der Burg |
| 2004/0034366 A1 | 2/2004 | Burg et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Tassel et al. |
| 2004/0133222 A1 | 8/2004 | Tran et al. |
| 2004/0167597 A1 | 8/2004 | Costantino |
| 2004/0172056 A1 | 9/2004 | Guterman |
| 2004/0181253 A1 | 9/2004 | Sepetka |
| 2004/0193246 A1 | 9/2004 | Ferrera |
| 2004/0254594 A1 | 12/2004 | Alfaro |
| 2004/0260332 A1 | 12/2004 | Dubrul |
| 2005/0021016 A1 | 1/2005 | Malecki et al. |
| 2005/0119684 A1 | 5/2005 | Gutterman |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0116709 A1 | 6/2006 | Sepetka |
| 2006/0116713 A1 | 6/2006 | Sepetka |
| 2006/0155323 A1 | 7/2006 | Porter et al. |
| 2006/0155367 A1 | 7/2006 | Hines |
| 2006/0167494 A1 | 7/2006 | Suddaby |
| 2006/0206199 A1 | 9/2006 | Churchwell et al. |
| 2007/0043391 A1 | 2/2007 | Moszner et al. |
| 2007/0106311 A1 | 5/2007 | Wallace et al. |
| 2007/0150045 A1 | 6/2007 | Ferrera |
| 2007/0173928 A1 | 7/2007 | Morsi |
| 2007/0198075 A1 | 8/2007 | Levy |
| 2007/0203567 A1 | 8/2007 | Levy |
| 2007/0208376 A1 | 9/2007 | Meng |
| 2007/0225760 A1 | 9/2007 | Moszner |
| 2007/0270902 A1 | 11/2007 | Slazas |
| 2007/0288083 A1 | 12/2007 | Hines |
| 2008/0045995 A1 | 2/2008 | Guterman |
| 2008/0097401 A1 | 4/2008 | Trapp |
| 2008/0097495 A1 | 4/2008 | Feller, III et al. |
| 2008/0119886 A1 | 5/2008 | Greenhalgh et al. |
| 2008/0147100 A1 | 6/2008 | Wallace |
| 2008/0221600 A1 | 9/2008 | Dieck et al. |
| 2009/0082803 A1 | 3/2009 | Adams |
| 2009/0099647 A1 | 4/2009 | Glimsdale et al. |
| 2009/0192455 A1 | 7/2009 | Ferrera |
| 2009/0209855 A1 | 8/2009 | Drilling et al. |
| 2009/0228029 A1 | 9/2009 | Lee |
| 2009/0281557 A1 | 11/2009 | Sander et al. |
| 2009/0297582 A1 | 12/2009 | Meyer |
| 2009/0318941 A1 | 12/2009 | Sepetka |
| 2010/0069948 A1 | 3/2010 | Veznedaroglu et al. |
| 2010/0174309 A1 | 7/2010 | Fulkerson |
| 2010/0217187 A1 | 8/2010 | Fulkerson |
| 2010/0256600 A1 | 10/2010 | Ferrera |
| 2010/0268204 A1 | 10/2010 | Tieu et al. |
| 2010/0318097 A1 | 12/2010 | Ferrera |
| 2011/0022149 A1 | 1/2011 | Cox |
| 2011/0040319 A1 | 2/2011 | Fulton, III |

(56) References Cited

U.S. PATENT DOCUMENTS

| | | |
|---|---|---|
| 2011/0046658 A1 | 2/2011 | Connor et al. |
| 2011/0054519 A1 | 3/2011 | Neuss |
| 2011/0082491 A1 | 4/2011 | Sepetka |
| 2011/0152993 A1 | 6/2011 | Marchand et al. |
| 2011/0160763 A1 | 6/2011 | Ferrera et al. |
| 2011/0190797 A1 | 8/2011 | Fulkerson |
| 2011/0202085 A1 | 8/2011 | Loganathan et al. |
| 2011/0264132 A1 | 10/2011 | Strauss |
| 2011/0319926 A1 | 12/2011 | Becking et al. |
| 2011/0319978 A1 | 12/2011 | Schaffer |
| 2012/0016406 A1 | 1/2012 | Ferrera |
| 2012/0041460 A1 | 2/2012 | Ferrera |
| 2012/0041475 A1 | 2/2012 | Ferrera |
| 2012/0071911 A1 | 3/2012 | Sadasivan |
| 2012/0150147 A1 | 6/2012 | Leynov |
| 2012/0165919 A1 | 6/2012 | Cox |
| 2012/0172973 A1 | 7/2012 | Deckard et al. |
| 2012/0271337 A1 | 10/2012 | Figulla et al. |
| 2012/0277788 A1 | 11/2012 | Cattaneo |
| 2012/0283768 A1 | 11/2012 | Cox et al. |
| 2012/0330341 A1 | 12/2012 | Becking et al. |
| 2012/0330347 A1 | 12/2012 | Becking |
| 2013/0035628 A1 | 2/2013 | Garrison et al. |
| 2013/0035712 A1 | 2/2013 | Theobald et al. |
| 2013/0066357 A1 | 3/2013 | Aboytes et al. |
| 2013/0066360 A1 | 3/2013 | Becking |
| 2013/0066413 A1 | 3/2013 | Jin |
| 2013/0090682 A1 | 4/2013 | Bachman et al. |
| 2013/0123830 A1 | 5/2013 | Becking |
| 2013/0165967 A1 | 6/2013 | Amin |
| 2013/0190800 A1 | 7/2013 | Murphy |
| 2013/0197622 A1 | 8/2013 | Mitra et al. |
| 2013/0245667 A1 | 9/2013 | Marchand |
| 2013/0274862 A1 | 10/2013 | Cox |
| 2013/0274866 A1 | 10/2013 | Cox |
| 2013/0274868 A1 | 10/2013 | Cox et al. |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0052233 A1 | 2/2014 | Cox |
| 2014/0163609 A1 | 6/2014 | Solem |
| 2014/0172001 A1 | 6/2014 | Becking et al. |
| 2014/0200607 A1 | 7/2014 | Sepetka et al. |
| 2014/0257360 A1 | 9/2014 | Keillor |
| 2014/0257374 A1 | 9/2014 | Heisel et al. |
| 2014/0277119 A1* | 9/2014 | Akpinar ............ A61B 17/12177 606/213 |
| 2014/0343602 A1 | 11/2014 | Cox et al. |
| 2014/0358178 A1 | 12/2014 | Hewitt et al. |
| 2015/0105817 A1 | 4/2015 | Marchand |
| 2015/0133990 A1 | 5/2015 | Davidson |
| 2015/0150563 A1 | 6/2015 | Marchand |
| 2015/0257763 A1 | 9/2015 | Blum et al. |
| 2015/0250628 A1 | 10/2015 | Monstadt |
| 2015/0272589 A1 | 10/2015 | Lorenzo |
| 2015/0313605 A1 | 11/2015 | Griffin |
| 2015/0351770 A1 | 12/2015 | Fulton, III |
| 2015/0351775 A1 | 12/2015 | Fulton, III |
| 2016/0011366 A1 | 4/2016 | Kobayashi et al. |
| 2016/0106437 A1 | 4/2016 | Van Der Burg |
| 2016/0120551 A1 | 5/2016 | Conner |
| 2016/0174991 A1 | 6/2016 | Chin |
| 2016/0206321 A1 | 7/2016 | Connor |
| 2016/0213380 A1 | 7/2016 | O'Brien |
| 2016/0249934 A1 | 9/2016 | Hewitt et al. |
| 2016/0249935 A1 | 9/2016 | Hewitt et al. |
| 2016/0345979 A1 | 12/2016 | Adams et al. |
| 2017/0128077 A1 | 5/2017 | Hewitt et al. |
| 2017/0156733 A1 | 6/2017 | Becking |
| 2017/0156734 A1 | 6/2017 | Griffin |
| 2017/0172581 A1 | 6/2017 | Bose |
| 2018/0125500 A1 | 5/2018 | Connor |
| 2018/0140305 A1 | 5/2018 | Connor |
| 2018/0193024 A1 | 7/2018 | Walzman |
| 2018/0193027 A1 | 7/2018 | Wang et al. |
| 2018/0193043 A1 | 7/2018 | Marchard et al. |
| 2018/0206848 A1 | 7/2018 | Walzman |
| 2018/0206851 A1 | 7/2018 | Walzman |
| 2018/0214158 A1 | 8/2018 | Walzman |
| 2018/0333248 A1 | 11/2018 | Davidson |
| 2019/0008522 A1 | 1/2019 | Lorenzo |
| 2019/0053810 A1 | 2/2019 | Griffin |
| 2019/0059909 A1 | 2/2019 | Griffin |
| 2019/0110796 A1 | 4/2019 | Jayaraman |
| 2019/0183519 A1 | 6/2019 | Imai et al. |
| 2019/0209146 A1 | 7/2019 | Hebert |
| 2019/0209178 A1 | 7/2019 | Richter |
| 2019/0216467 A1 | 7/2019 | Goyal |
| 2019/0223876 A1 | 7/2019 | Badruddin |
| 2019/0223881 A1 | 7/2019 | Hewitt |
| 2019/0231328 A1 | 8/2019 | Hebert |
| 2019/0262002 A1 | 8/2019 | Benjamin |
| 2019/0269414 A1 | 9/2019 | Griffin |
| 2019/0274691 A1 | 9/2019 | Sepetka |
| 2019/0336132 A1 | 11/2019 | Warner |
| 2019/0343533 A1 | 11/2019 | Costalat |
| 2019/0357914 A1 | 11/2019 | Gorochow |
| 2019/0365472 A1 | 12/2019 | Connor |
| 2019/0374228 A1 | 12/2019 | Wallace |
| 2019/0380718 A1 | 12/2019 | Morsi |
| 2019/0388108 A1 | 12/2019 | Ferrera |
| 2020/0029973 A1 | 1/2020 | Walzman |
| 2020/0038032 A1 | 2/2020 | Rhee |
| 2020/0038035 A1 | 2/2020 | Griffin |
| 2020/0054344 A1 | 2/2020 | Connor |
| 2020/0060702 A1 | 2/2020 | Davidson |
| 2020/0069313 A1 | 3/2020 | Xu |
| 2020/0093499 A1 | 3/2020 | Lorenzo |
| 2020/0100795 A1 | 4/2020 | Connor |
| 2020/0113576 A1 | 4/2020 | Gorochow |
| 2020/0138422 A1 | 5/2020 | Hebert |
| 2020/0155333 A1 | 5/2020 | Franano |
| 2020/0163784 A1 | 5/2020 | Franano |
| 2020/0187952 A1 | 6/2020 | Walsh |
| 2020/0187978 A1 | 8/2020 | Walzman |
| 2020/0253766 A1 | 8/2020 | Walzman |
| 2020/0268365 A1 | 8/2020 | Hebert |
| 2020/0281603 A1 | 9/2020 | Marchand |
| 2020/0289124 A1 | 9/2020 | Rangwala |
| 2020/0289125 A1 | 9/2020 | Dholakia |
| 2020/0289126 A1 | 9/2020 | Hewitt |
| 2020/0305886 A1 | 10/2020 | Soto Del |
| 2020/0323534 A1 | 10/2020 | Shimizu |
| 2020/0337710 A1 | 10/2020 | Lorenzo |
| 2020/0340154 A1 | 10/2020 | Koppe |
| 2020/0345376 A1 | 11/2020 | Fulton, III |
| 2020/0367894 A1 | 11/2020 | Pereira |
| 2020/0367896 A1 | 11/2020 | Zaidat |
| 2020/0367897 A1 | 11/2020 | Wolfe |
| 2020/0367904 A1 | 11/2020 | Becking |
| 2020/0375606 A1 | 12/2020 | Lorenzo |
| 2020/0375607 A1 | 12/2020 | Soto Del Valle |
| 2020/0390455 A1 | 12/2020 | Nguyen et al. |
| 2020/0397447 A1 | 12/2020 | Lorenzo |
| 2020/0405347 A1 | 12/2020 | Walzman |
| 2021/0007755 A1 | 1/2021 | Lorenzo |
| 2021/0022765 A1 | 1/2021 | Walzman |
| 2021/0045750 A1 | 2/2021 | Wolfe |
| 2021/0077116 A1 | 3/2021 | Ferrera |
| 2021/0106337 A1 | 4/2021 | Hewitt |
| 2021/0128160 A1 | 5/2021 | Li |
| 2021/0128161 A1 | 5/2021 | Nageswaran |
| 2021/0128162 A1 | 5/2021 | Rhee |
| 2021/0128165 A1 | 5/2021 | Pulugurtha |
| 2021/0128166 A1 | 5/2021 | Kealey |
| 2021/0128167 A1 | 5/2021 | Patel |
| 2021/0128168 A1 | 5/2021 | Nguyen |
| 2021/0128169 A1 | 5/2021 | Li |
| 2021/0129275 A1 | 5/2021 | Nguyen |
| 2021/0137530 A1 | 5/2021 | Greene, Jr. et al. |
| 2021/0145449 A1 | 5/2021 | Gorochow |
| 2021/0153871 A1 | 5/2021 | Griffin |
| 2021/0153872 A1 | 5/2021 | Nguyen et al. |

(56) References Cited

U.S. PATENT DOCUMENTS

| | | | |
|---|---|---|---|
| 2021/0169496 A1 | 6/2021 | Badruddin et al. |
| 2021/0169499 A1 | 6/2021 | Merritt et al. |
| 2021/0186518 A1 | 6/2021 | Gorochow et al. |
| 2021/0196284 A1 | 7/2021 | Gorochow et al. |
| 2021/0204955 A1 | 7/2021 | Wallace et al. |
| 2021/0219982 A1 | 7/2021 | Badruddin et al. |
| 2021/0251635 A1 | 8/2021 | Soto Del Valle et al. |
| 2021/0259719 A1 | 8/2021 | Griffin |
| 2021/0275184 A1 | 9/2021 | Hewitt et al. |
| 2021/0275188 A1 | 9/2021 | Plaza et al. |
| 2021/0282784 A1 | 9/2021 | Sepetka et al. |
| 2021/0282786 A1 | 9/2021 | Zaidat et al. |
| 2021/0330331 A1 | 10/2021 | Lorenzo |
| 2021/0346032 A1 | 11/2021 | Patterson et al. |
| 2021/0361290 A1 | 11/2021 | Badruddin et al. |
| 2021/0378646 A1 | 12/2021 | Amplatz et al. |
| 2021/0401439 A1 | 12/2021 | Lorenzo et al. |
| 2022/0022884 A1 | 1/2022 | Wolf et al. |
| 2022/0022886 A1 | 1/2022 | Becking et al. |
| 2022/0054141 A1 | 2/2022 | Zaidat et al. |
| 2022/0054286 A1 | 2/2022 | Goyal |

FOREIGN PATENT DOCUMENTS

| | | |
|---|---|---|
| CN | 102940514 | 3/2013 |
| CN | 103099652 | 5/2013 |
| CN | 103142261 | 6/2013 |
| CN | 104168843 | 11/2014 |
| CN | 104958087 | 10/2015 |
| CN | 204931771 | 1/2016 |
| CN | 204971420 | 1/2016 |
| CN | 106456183 | 2/2017 |
| DE | 102008028308 | 4/2009 |
| DE | 102008015781 | 9/2011 |
| DE | 102011102955 | 12/2012 |
| DE | 102009058132 | 7/2014 |
| DE | 202008018523 | 4/2015 |
| DE | 102013106031 | 7/2015 |
| DE | 102012107175 | 8/2015 |
| DE | 102012102844 | 3/2020 |
| DE | 102019121546 | 2/2021 |
| DE | 102019121554 | 2/2021 |
| EP | 0836450 | 4/1998 |
| EP | 0902704 | 3/1999 |
| EP | 1003422 | 5/2000 |
| EP | 1295563 | 3/2003 |
| EP | 1441649 | 8/2004 |
| EP | 1483009 | 12/2004 |
| EP | 1494619 | 1/2005 |
| EP | 1527753 | 9/2005 |
| EP | 1569565 | 9/2005 |
| EP | 1574169 | 9/2005 |
| EP | 1054635 | 11/2005 |
| EP | 1610666 | 1/2006 |
| EP | 1633275 | 3/2006 |
| EP | 1651117 | 5/2006 |
| EP | 1659988 | 5/2006 |
| EP | 1725185 | 11/2006 |
| EP | 1804719 | 7/2007 |
| EP | 1862122 | 12/2007 |
| EP | 1923005 | 5/2008 |
| EP | 1923019 | 5/2008 |
| EP | 2063791 | 6/2009 |
| EP | 2134263 | 12/2009 |
| EP | 2157937 | 3/2010 |
| EP | 2207500 | 7/2010 |
| EP | 2265193 | 12/2010 |
| EP | 2266465 | 12/2010 |
| EP | 2279023 | 2/2011 |
| EP | 2324775 | 5/2011 |
| EP | 2349024 | 8/2011 |
| EP | 2367482 | 9/2011 |
| EP | 2387951 | 11/2011 |
| EP | 2399524 | 12/2011 |
| EP | 2460476 | 6/2012 |
| EP | 2460478 | 6/2012 |
| EP | 2468349 | 6/2012 |
| EP | 2496299 | 9/2012 |
| EP | 2506808 | 10/2012 |
| EP | 2543345 | 1/2013 |
| EP | 2567663 | 3/2013 |
| EP | 2596754 | 5/2013 |
| EP | 2613709 | 7/2013 |
| EP | 2617386 | 7/2013 |
| EP | 2618709 | 7/2013 |
| EP | 2647343 | 10/2013 |
| EP | 2677944 | 1/2014 |
| EP | 2744412 | 6/2014 |
| EP | 2848211 | 3/2015 |
| EP | 2854704 | 4/2015 |
| EP | 2887887 | 7/2015 |
| EP | 2923674 | 9/2015 |
| EP | 2926744 | 10/2015 |
| EP | 2943152 | 11/2015 |
| EP | 2964105 | 1/2016 |
| EP | 3068337 | 9/2016 |
| EP | 3082619 | 10/2016 |
| EP | 3131515 | 2/2017 |
| EP | 3136986 | 3/2017 |
| EP | 3148481 | 4/2017 |
| EP | 3151904 | 4/2017 |
| EP | 3171793 | 5/2017 |
| EP | 3187117 | 7/2017 |
| EP | 3247285 | 11/2017 |
| EP | 3261703 | 1/2018 |
| EP | 1998686 | 2/2018 |
| EP | 2460477 | 4/2018 |
| EP | 3345553 | 7/2018 |
| EP | 2806825 | 8/2018 |
| EP | 2753246 | 11/2018 |
| EP | 3413808 | 12/2018 |
| EP | 3429479 | 1/2019 |
| EP | 3456271 | 3/2019 |
| EP | 3456272 | 3/2019 |
| EP | 3501429 | 6/2019 |
| EP | 2254505 | 7/2019 |
| EP | 3510945 | 7/2019 |
| EP | 3512459 | 7/2019 |
| EP | 3517055 | 7/2019 |
| EP | 2194885 | 11/2019 |
| EP | 3572010 | 11/2019 |
| EP | 3173037 | 12/2019 |
| EP | 3574851 | 12/2019 |
| EP | 3585275 | 1/2020 |
| EP | 3600068 | 2/2020 |
| EP | 3622901 | 3/2020 |
| EP | 3628242 | 4/2020 |
| EP | 3636173 | 4/2020 |
| EP | 2405820 | 6/2020 |
| EP | 3669800 | 6/2020 |
| EP | 3677192 | 7/2020 |
| EP | 3714812 | 9/2020 |
| EP | 2244666 | 11/2020 |
| EP | 3153114 | 11/2020 |
| EP | 3740138 | 11/2020 |
| EP | 3755276 | 12/2020 |
| EP | 3501428 | 4/2021 |
| EP | 3568088 | 4/2021 |
| EP | 3808284 | 4/2021 |
| EP | 3821825 | 5/2021 |
| EP | 3838186 | 6/2021 |
| EP | 3865079 | 8/2021 |
| EP | 3908208 | 11/2021 |
| EP | 3908209 | 11/2021 |
| EP | 3908354 | 11/2021 |
| FR | 3061647 | 6/2020 |
| IL | 248515 | 7/2019 |
| JP | H02150481 | 6/1990 |
| JP | H0447415 | 4/1992 |
| JP | H0850701 I | 7/1996 |
| JP | 2003-175113 | 6/2003 |
| JP | 2005028863 | 2/2005 |
| JP | 2005537092 | 12/2005 |
| JP | 2006509578 | 3/2006 |

(56) References Cited

FOREIGN PATENT DOCUMENTS

| | | |
|---|---|---|
| JP | 2010500187 | 1/2010 |
| JP | 2012-501793 | 1/2012 |
| JP | 2012030497 | 2/2012 |
| JP | 2013-027592 | 2/2013 |
| JP | 2013-509914 | 3/2013 |
| JP | 2013537069 | 9/2013 |
| RU | 2018131107 | 10/2018 |
| RU | 2019120682 | 9/2019 |
| RU | 2704539 | 10/2019 |
| RU | 2018145502 | 6/2020 |
| RU | 2018145543 | 6/2020 |
| RU | 2019110988 | 10/2020 |
| RU | 2019115837 | 11/2020 |
| RU | 2019116175 | 11/2020 |
| RU | 2019127900 | 3/2021 |
| RU | 2019129351 | 3/2021 |
| RU | 2019129526 | 3/2021 |
| WO | 2006/034149 | 3/2006 |
| WO | 2006/052322 | 5/2006 |
| WO | 2007/076480 | 7/2007 |
| WO | 2007/079402 | 7/2007 |
| WO | 2008/036156 | 3/2008 |
| WO | 2008/151204 | 12/2008 |
| WO | 2009/052432 | 4/2009 |
| WO | 2009/132045 | 10/2009 |
| WO | 2009/135166 | 11/2009 |
| WO | 2010/030991 | 3/2010 |
| WO | 2010/134914 | 11/2010 |
| WO | 2011/057002 | 5/2011 |
| WO | 2012/032030 | 3/2012 |
| WO | 2012/034135 | 3/2012 |
| WO | 2012/099704 | 7/2012 |
| WO | 2012/099909 | 7/2012 |
| WO | 2012/099910 | 7/2012 |
| WO | 2012/135037 | 10/2012 |
| WO | 2012/163880 | 12/2012 |
| WO | 2013/005195 | 1/2013 |
| WO | 2013/016618 | 1/2013 |
| WO | 2013/028579 | 2/2013 |
| WO | 2013/103888 | 7/2013 |
| WO | 2013/109309 | 7/2013 |
| WO | 2012/113554 | 8/2013 |
| WO | 2013/152327 | 10/2013 |
| WO | 2013/184595 | 12/2013 |
| WO | 2014/029835 | 2/2014 |
| WO | 2015/095538 | 6/2015 |
| WO | 2015/160721 | 10/2015 |
| WO | 2015/166013 | 11/2015 |
| WO | 2015/184075 | 12/2015 |
| WO | 2015/187196 | 12/2015 |
| WO | 2016/107357 | 7/2016 |
| WO | 2016/118420 | 7/2016 |
| WO | 2016/137997 | 9/2016 |
| WO | 2017/106567 | 6/2017 |
| WO | 2017/139702 | 8/2017 |
| WO | 2017/156275 | 9/2017 |
| WO | 2017/161283 | 9/2017 |
| WO | 2018/051187 | 3/2018 |
| WO | 2018/130624 | 7/2018 |
| WO | 2018/156833 | 8/2018 |
| WO | 2018/175221 | 9/2018 |
| WO | 2019/143755 | 7/2019 |
| WO | 2019/165360 | 8/2019 |
| WO | 2020/139544 | 7/2020 |
| WO | 2020/150023 | 7/2020 |
| WO | 2020/190620 | 9/2020 |
| WO | 2020/190630 | 9/2020 |
| WO | 2020/190639 | 9/2020 |
| WO | 2020/243039 | 12/2020 |
| WO | 2021/028160 | 2/2021 |
| WO | 2021/028161 | 2/2021 |
| WO | 2021/051110 | 3/2021 |
| WO | 2021/087610 | 5/2021 |
| WO | 2021/092620 | 5/2021 |
| WO | 2021/183793 | 9/2021 |

OTHER PUBLICATIONS

Altes et al., "Creation of Saccular Aneurysms in the Rabbit: A Model Suitable for Testing Endovascular Devices," AJR Arn J Roentgenol, 2000, 174(2):349-354.

Blackshear et al., "Appendage obliteration to reduce stroke in c<irdiac surgical patients v. th atrial fibrillation," Ann. Thorac. Surg., Feb. 1996, 61(2):755-9.

CN Office Action in Chinese Appln. No. 201780024233.7, dated Jul. 9, 2020, 20 pages (with English Translation).

EP Extended European Search Report in European Appln. No. 17710255.5, dated Nov. 12, 2020. 13 pages.

Gottlieb et al., "Anticoagulation in atrial fibrillation. Does efficacy in clinical trials translate into effectiveness in practice?" Arch. Intern. Med., Sep. 1994, 154(17):1945-53.

JP Office Action in Japanese Appln. 2017-508761, dated Nov. 27, 2018, 4 pages (English titillation).

JP Office Action in Japanese Appln. No. 2017-508761, dated Mar. 19, 2019, 3 pages (English translation).

JP Office Action in Japanese Appln. No. 2018-529554, dated Nov. 30, 2020, 11 pages (with English translation).

PCT Form ISA/206—Invitation To Pay Additional Fees in International Appln. PCT/EP2016/080152, dated Feb. 24, 2017, 9 pages.

PCT International Preliminary Report on Patentability in International Appln. No. PCT/EP2019/072576, dated Feb. 25, 2020, 12 pages.

PCT International Preliminary Report on Patentabilityl in International Appln. PCT/EP2015/059429, dated Jul. 13, 2016, 11 pages.

International Search Report and Written Opinion in International Appln. No. PCT/EP2018/072576, dated Nov. 21, 2018, 20 pages.

International Search Report and Written Opinion in International Application No. PCT!EP2016/080152, dated Jun. 16, 2017, 8 pages.

PCT International Search Report in International Appln. PCT/EP2015/059429, dated Jul. 6, 2015, 5 pages.

Schaffer, "Biocompatible Wire," Advanced Materials & Processes, Oct. 2002, pp. 51-54.

Bosworth et al., "Gamma irradiation of electrospun poly(£-caprolactone) fibers affects material properties but not cell response," Journal of Polymer Science Part B: Polymer Physics, Apr. 2012, pp. 870-876.

CA Office Action in Canadian Appl. No. 2,946,078, dated May 26, 2021, 4 pages.

CN Office Action in Chinese Appln. No. 201580035663.X, dated Aug. 1, 2018, 27 pages (with English Translation).

CN Office Action in Chinese Appln. No. 201780024233.7, dated Oct. 22, 2020, 17 pages (with English Translation).

EP Extended Search Report in European Appln. No. 19159876.2, dated Jun. 14, 2019, 9 pages.

EP Extended Search Report in European Appln. No. 20201759.6, dated Nov. 12, 2020, 12 pages.

EP Office Action in European AppIn No. 16808631.2, dated Aug. 16, 2019, 8 pages.

Izadi et al., "Teflon hierarchical nanopillars with dry and wet adhesive properties," Journal of Polymer Science Part B: Polymer Physics, Apr. 2012, pp. 846-851.

Ohta et al., "Size control of phase-separated liquid crystal droplets in a polymer matrix based on the phase diagram," Journal of Polymer Science Part B: Polymer Physics, Apr. 2012, pp. 863-869.

Popov et al., "Interacting nanoparticles with functional surface groups," Journal of Polymer Science Part B: Polymer Physics, Mar. 2012, pp. 852-862.

JP Office Action in Japanese Appln. No. 2018-529554, dated Jul. 12, 2021, 6 pages (with English translation).

JP Office Action in Japanese Appln. No. 2018-529554, dated Sep. 15, 2020, 6 pages (with English translation).

JP Office Action in Japanese Application No. 2019-145966, dated Sep. 1, 2020, 6 pages (with English translation).

PCT International Preliminary Report on Patentability in International Application No. PCT/EP2016/080152, dated Jun. 12, 2018, 10 pages.

(56) References Cited

OTHER PUBLICATIONS

PCT International Preliminary Report on Patentability in International Application No. PCT/EP2017/055765, dated Sep. 11, 2018, 9 pages.
PCT International Written Opinion in International Application No. PCT/EP2021/054103, dated Aug. 26, 2021, 4 pages.
CN Office Action in Chinese Appln. No. 201780024233.7, dated Apr. 22, 2021, 6 pages.
International Search Report in International Appln. No. PCT/EP2017/055765 dated Apr. 18, 2017, 5 pages.

* cited by examiner

OCCLUSION DEVICE

CROSS-REFERENCE TO RELATED APPLICATIONS

This application is a continuation of U.S. patent application Ser. No. 16/952,756, filed Nov. 19, 2020, now U.S. Pat. No. 11,648,013, which is a continuation of U.S. Patent Application of U.S. Ser. No. 16/080,626, filed Aug. 28, 2018, now U.S. Pat. No. 10,869,672, issued Dec. 22, 2020, which is a U.S. National Phase Application under 35 U.S.C. § 371 of International Application PCT/EP2017/055765, filed on Mar. 13, 2017, which claims priority to U.S. Provisional Patent Application 62/307,137, filed Mar. 11, 2016, all of which are incorporated by reference.

FIELD OF THE INVENTION

The present invention relates generally to the field of occlusion devices and/or occlusion device systems and/or implantable occlusion devices and the treatment and/or amelioration of Left Atrial Appendage (LAA).

BACKGROUND OF THE DISCLOSURE

Left Atrial Appendage (LAA) or left auricle or auricula or left auricle appendix is a muscular pouch or wind-sock like structure projecting from the left atrium of the heart. During the disease pathology of atrial fibrillation (AF) or mitral valve disease or other heart conditions, blood clots can form in the LAA. For example, 10-20% of patients afflicted with AF will present with blood clot formation in the LAA. It is now known that 90% of the blood clots that form as a result of AF, form in the LAA. Blackshear J L, Odell J A (Feb. 1996) *Ann. Thorac. Surg.* 61 (2): 755-9. Such blood clots pose the risk of dislodging and becoming embolic material which may pose significant risks relating to stroke or other ischemic damage to the body's organs. As such, LAA occlusion treatment techniques are a viable option to the prevention of stroke in AF or other disorders involving blood clot formation in the LAA.

LAA occlusion is an alternative treatment strategy to blood clotting drugs or anticoagulants such as in the class of coumarin-type drugs, heparin-based drugs, small molecule inhibitor drugs, antithrombin protein-based drugs, and/or the like. Not all patients are suitable candidates for such blood clotting medicines due to underlying issues relating to prior bleeds, non-compliance, and/or pregnancy (17% of patients in one study: Gottlieb L K, Salem-Schatz S (Sep. 1994) *Arch. Intern. Med.* 154 (17): 1945-53), and are therefore in need of other treatment options such as the use of occlusion device strategies.

Current devices for LAA occlusion generally include an expandable nitinol frame or the like. One such catheter-based device comprises a body designed to occlude an LAA and a retention member secured to the body. However, while the use of such devices results in less hemorrhagic stroke than with anticoagulants alone, there are known disadvantages and limitations such as, without limitation, pericardial effusion, LAA closure, dislodgement of the device, blood clot formation on the device, anatomical incompatibilities and/or a combination thereof. Accordingly, there is a need for improved occlusion devices in the field.

While such occlusion devices may be found, for example in U.S. Pat. Nos. 5,025,060; 5,496,277; 5,928,260; 6,152, 144; 6,168,622; 6,221,086; 6,334,048; 6,419,686; 6,506, 204; 6,605,102; 6,589,256; 6,663,068; 6,669,721; 6,780, 196; 7,044,134; 7,093,527; 7,128,073; 7,128,736; 7,152, 605; 7,410,482; 7,722,641; 7,229,461; 7,410,482; 7,597, 704; 7,695,488; 8,034,061; 8,080,032; 8,142,456; 8,261, 648; 8,262,692; 8,361,138; 8,430,012; 8,454,633; 8,470, 013; 8,500,751; 8,523,897; and 8,535,343; and United States Application Numbers 2003/0195553; 2004/0098027; 2006/0167494; 2006/0206199; 2007/0288083; 2008/0147100; 2008/0221600; 2010/0069948; 2011/0046658; 2012/0172973; 2012/0283768; 2012/0330341; 2013/0035712; 2013/0090682; 2013/0197622; 2013/0274868; and 2014/0005714; European Application Number EP 1651117; and International Application Numbers WO13/028579; WO13/109309; WO13/152327; none of these references disclose the embodiments of the occlusion device disclosed herein.

Reference is also made to commonly owned, U.S. patent application Ser. No. 14/699,188; which discloses a device for treating endovascular disease, and which is incorporated herein by reference in its entirety.

Therefore, disclosed herein are innovative improvements and several advantages in the field of occlusion devices because the occlusion device disclosed herein provides LAA treatment and/or amelioration while promoting more effective endothelialization around the device. Accordingly, an improved LAA occlusion device as disclosed herein maximizes shielding of blood flow into the left atrial appendage and traps any clot inside. Additionally, the occlusion device disclosed herein has an open mesh density which permits enhanced tissue integration and stabilization of the device. Other advantages include, without limitation, elimination of the need to place large numbers of coils or framing wires or nitinol cages in the LAA pouch and the cost-effectiveness relating thereto; a higher level of compatibility with challenging anatomies that are incompatible with current devices requiring significant real estate in the left atrium space adjacent to the LAA; and significant time-saving opportunities from the use of a single implant.

All documents and references cited herein and in the referenced patent documents, are hereby incorporated herein by reference.

SUMMARY OF THE INVENTION

The present inventor has designed an occlusion device for providing LAA treatment. As such, an occlusion device of the present invention is for promoting stabilization and more effective endothelialization around the device and is configured for maximizing shielding of blood flow into the LAA and traps any clot inside.

Disclosed herein is an occlusion device comprising: (a) a substantially solid marker band having an inner and outer diameter, a proximal end, and a distal end; and (b) a resilient mesh body attached within the marker band, wherein the body is a length y, and wherein the body comprises a bolus of additional resilient mesh material of a length x, wherein y is greater than x, and wherein the body extends distally from the marker band and the body has a first delivery shape and a second expandable deployed shape.

In one embodiment, the resilient mesh body comprises a dual layer of mesh. In a further embodiment, the dual layer of mesh is a circumferentially folded dual layer of mesh.

In one embodiment, the resilient mesh body has an open mesh density for enhanced tissue integration and/or stabilization of the occlusion device.

In another embodiment, the resilient mesh body and the bolus of additional resilient mesh material are dissimilar metals.

In another embodiment, the resilient mesh body is constructed from a super elastic material. In a further embodiment, the resilient mesh body is constructed from nitinol. In yet another embodiment, the resilient mesh body is constructed from DFT platinum core nitinol.

In another embodiment, the bolus of additional resilient mesh is constructed from a super elastic material. In a further embodiment, the bolus of additional resilient mesh is constructed from nitinol. In yet another embodiment, the bolus of additional resilient mesh is constructed from DFT platinum core nitinol.

In another embodiment, the marker band comprises a rigid member.

In another embodiment, the marker band comprises a rigid member selected from the group consisting of a ring, collar, and suture.

In another embodiment, the marker band is reinforced.

In another embodiment, the occlusion device is a Left Atrial Appendage (LAA) occlusion device.

Also disclosed herein is a kit comprising the occlusion device disclosed herein and a delivery means for deploying the occlusion device.

Additionally disclosed herein are methods for manufacture and/or delivery and/or deployment of the occlusion device disclosed herein.

In other embodiments, the occlusion device in the preceding paragraphs may incorporate any of the preceding or subsequently disclosed embodiments.

The Summary of the Invention is not intended to define the claims nor is it intended to limit the scope of the invention in any manner.

Other features and advantages of the invention will be apparent from the following Drawings, Detailed Description, and the Claims.

DETAILED DESCRIPTION

The present invention is illustrated in the drawings and description in which like elements are assigned the same reference numerals. However, while particular embodiments are illustrated in the drawings, there is no intention to limit the present invention to the specific embodiment or embodiments disclosed. Rather, the present invention is intended to cover all modifications, alternative constructions, and equivalents falling within the spirit and scope of the invention. As such, the drawings are intended to be illustrative and not restrictive.

Unless otherwise defined, all technical terms used herein have the same meaning as commonly understood by one of ordinary skill in the art to which this technology belongs.

Example implementations of the LAA occlusion device disclosed herein provide treatment and/or amelioration of LAA. Such an occlusion device is delivered intravascularly to the LAA site (pouch and/or cavity) via a catheter or other modes of delivery such that the deployed shape of the occlusion device forms a liner that at least seals the opening and/or inside of the LAA pouch, the substantially solid marker band traverses the opening of the LAA pouch or cavity while promoting more effective endothelialization around the device.

In an exemplary method of delivery of an occlusion device disclosed herein, a catheter is introduced into the left atrial space having a left atrial appendage (LAA), wherein there is formation of a blood clot or clots. The LAA generally includes the opening (or neck) of the LAA and the muscular pouch or cavity of the LAA. The catheter tip is positioned adjacent the opening of the LAA such that the occlusion device can be deployed. The occlusion device disclosed herein is configured of resilient mesh capable of expansion in a low profile manner, in the manner of an inverted mushroom, to effectively line the inside of the LAA pouch thereby occluding the LAA through promoting endothelialization around the device.

For the purposes of the disclosure herein, the terminology "low profile" means that the resilient mesh body of the device, in free air, has a height that is about 10-20% of its width, and therefore in its deployed shape the resilient mesh body, even though expanded, lay flush, in a flattened manner as in an inverted mushroom, up against the tissue walls of the LAA cavity such that it is positioned to cover at least partially, the interior surface of the LAA cavity. As such the opening and/or inside of the LAA pouch or cavity is sealed thereby occluding the LAA.

For the purposes of the disclosure herein, the terminology "corresponds to" means there is a functional and/or mechanical relationship between objects which correspond to each other. For example, an occlusion device delivery system corresponds to (or is compatible with) an occlusion device for deployment thereof.

For the purposes of the disclosure herein, the terminology "occlusion device" means and/or may be interchangeable with terminology such as, without limitation, "device" or "occlusion device system" or "occlusion system" or "system" or "occlusion device implant" or "implant" and the like.

Occlusion device delivery systems are well known and readily available in the art. For example, such delivery technologies may be found, without limitation, in U.S. Patent and Publication Nos. U.S. Pat. Nos. 4,991,602; 5,067,489; 6,833,003; 2006/0167494; and 2007/0288083; each of the teachings of which are incorporated herein. For the purposes of the present invention, any type of occlusion device delivery means and/or delivery system and/or delivery technology and/or delivery mechanism and/or detachment (and/or attachment) means and/or detachment system and/or detachment technology and/or detachment mechanism may be utilized and/or modified in such a manner as to make it compatible (so as to correspond) with the occlusion device disclosed herein. Exemplary occlusion device delivery mechanisms and/or systems include, without limitation, guide wires, pusher wires, catheters, micro-catheters, and the like. Exemplary occlusion device detachment mechanisms include, without limitation, fluid pressure, electrolytic mechanisms, hydraulic mechanisms, interlocking mechanisms, and the like. In one embodiment, the occlusion device disclosed herein is used in a method of electrolytic detachment. Electrolytic detachment is well known in the art and can be found, for example, in U.S. Pat. Nos. 5,122,136; 5,423,829; 5,624,449; 5,891,128; 6,123,714; 6,589,230; and 6,620,152.

Figure 1:
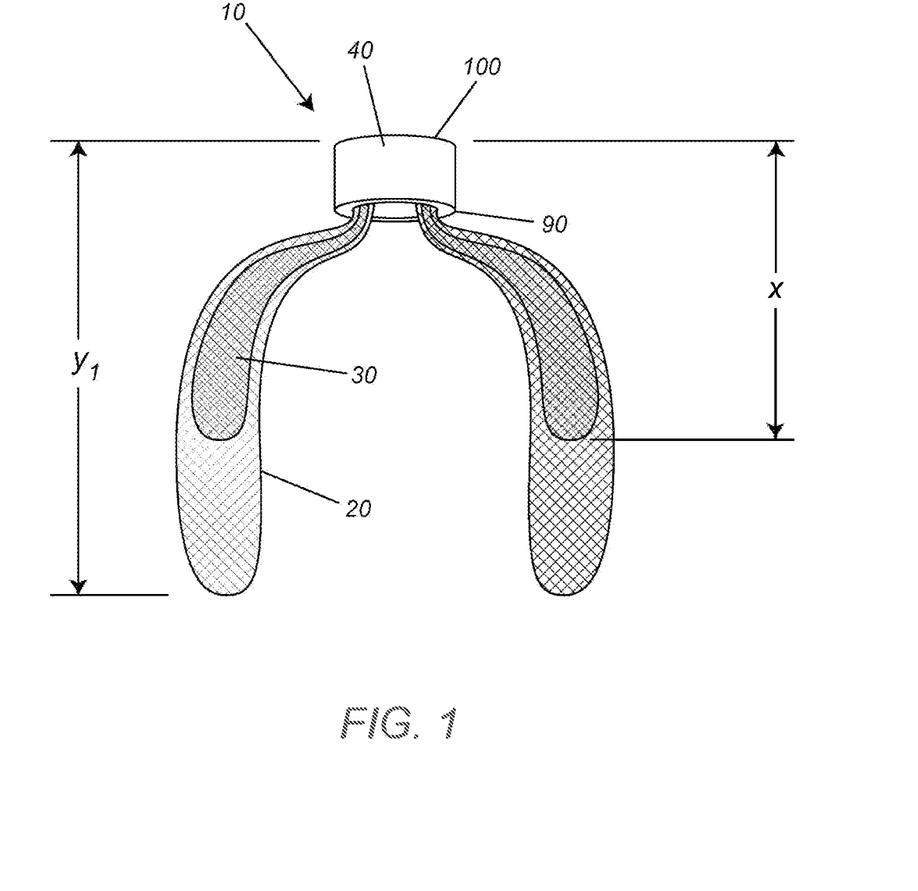
FIG. 1 illustrates a cross section of an embodiment of the occlusion device disclosed herein for LAA treatment.
Figure 2:
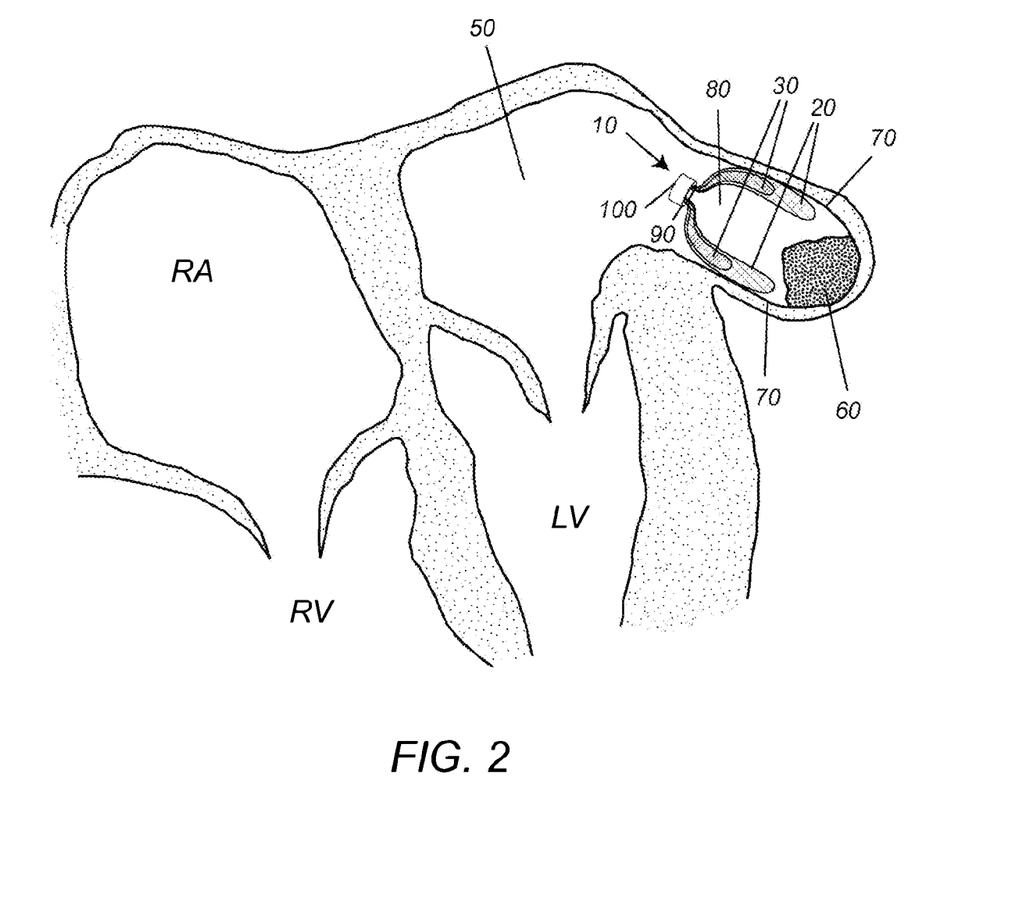
FIG. 2 illustrates an embodiment of the occlusion device disclosed herein deployed in a LAA pouch or cavity.

Exemplary embodiments of the occlusion device disclosed herein are depicted in FIGS. 1-2.

FIG. 1 shows an exemplary embodiment of an occlusion device as disclosed herein for promoting more effective endothelialization around the device. The occlusion device disclosed herein is configured of resilient mesh capable of expansion to effectively line (or coat) the inside of the LAA pouch thereby occluding the LAA through promoting endothelialization around the device. The occlusion device herein comprises a resilient mesh 20 body comprised of a circumferentially folded over single layer of mesh to create a dual layer of mesh. Such a 20 body extends distally from the 40 marker band and has a length y. The ends of the dual layer of mesh are attached within the 40 marker band. In one embodiment, the ends of the mesh are attached at the 90 proximal end of the 40 marker band and the 20 body extends distally. In another embodiment, the ends of the mesh are attached at the 100 distal end and the 20 body extends distally. The 20 body comprises within it a 30 bolus (additional mesh mass) of resilient mesh material of length x. In such an exemplary configuration of the occlusion device disclosed and illustrated herein, y is greater than x. Even in the expanded or deployed shape of the device, the 20 body maintains a low profile shape with respect to the LAA 50 pouch and inside which the 20 body of the device resides (and lines the LAA tissue 70 walls) upon deployment. As is accepted in the art, the x and y measurements in length of such an occlusion device are measured in free air. An exemplary range of the length (y) of the occlusion device 20 body is approximately 20-50 millimeters (mm) and an exemplary length (x) of the 30 bolus comprised within the 20 body is less than the value of length y. In one embodiment, the resilient mesh 20 body is attached inside/within the substantially solid 40 marker band and the 20 body extend distally from the 40 marker band. Such a configuration of the 40 marker band with respect to the 20 body confers the capability of the device to seal the 80 opening of the LAA and as such effectively occlude the LAA.

FIG. 2 shows an exemplary embodiment of an occlusion device as disclosed herein for treating and/or ameliorating LAA as deployed in the LAA 50 pouch. Such a configuration as illustrated in both FIG. 1 and FIG. 2 confers the capability of the device to seal the 80 opening of the LAA pouch and effectively occlude the LAA. In this embodiment, the mesh 20 body of the device lines, as in a low profile manner (lays flat against in the manner of an inverted mushroom), the LAA 70 walls. Accordingly, even in the deployed shape of the device disclosed herein and as also shown in FIG. 2, distance y is greater than distance x. In one embodiment, a size 12F catheter or smaller is used for deployment of the device disclosed herein. In another embodiment, electrolytic delivery and/or deployment and/or detachment via an electrolytic wire through the left atrial space adjacent to the LAA is used for the device disclosed herein. Electrolytic detachment means and methods such as those disclosed in U.S. Pat. No. 5,122,136 are well known in the art.

The low profile deployed shape of the 20 body of the device provides an anchor for the occlusion device without adversely interfering with fluid flow through left atrial space. This mechanism of action allows for the mesh 20 body's dual layer, expandable in it's deployed form in the manner of an inverted mushroom, to line the inner 70 walls of the LAA 50 pouch and facilitate endothelial growth through the open mesh density created by the mesh 20 body and its 30 bolus of additional mesh within the mesh body. Endothelialization around the device and/or endothelial growth around the 20 body of the device is triggered because such a configuration maximizes shielding of blood flow into the LAA and traps any 60 clot inside. The combination of the 30 bolus of mesh within the 20/30 dual mesh layer of the body causes the device to function in the LAA as an effective shield, i.e., as an enhanced area of coverage at the cap of the implant which further reduces blood flow. Such a device also functions as a stabilizer and prevents transfer of movement or forces through the mesh during expansion. This has several advantages including, without limitation, anchoring the device, providing undisturbed fluid flow, and/or facilitating neointimal development across the 80 opening of LAA, all without requiring any additional material (mesh or otherwise) in the left atrial space. As such, there is no additional mesh material component, other than the mesh 20 body comprising the 30 bolus of additional mesh within the 20 body and extending from the 40 marker band necessary for the device to anchor or stabilize within the LAA.

Such a configuration facilitates sealing of the 80 opening of the LAA and therefore 60 clot formation and/or healing and/or shrinkage of the LAA 50 pouch which is particularly advantageous if the size or mass of the 60 clot is causing pain or other side effects within the patient. Such a configuration is also advantageous because it requires a minimum amount of resilient mesh material thereby eliminating the need to fill or substantially fill, in a spherical, radially expanded manner, the space in the LAA 50 pouch. Such an occlusion device is also well suited for conformability across a broad range of LAA morphologies, particularly since it is well known and generally accepted that LAAs vary considerably in size and are not perfectly round in shape. Advantageously, because an occlusion device as disclosed herein, has a minimum of or less material than the current standard devices, this minimizes the need for anticoagulation therapy and/or lessens the risk of clot emboli formation.

In another embodiment of an occlusion device disclosed herein, the resilient mesh 20 body of resilient mesh comprises a relatively uniform distribution of wire mesh strands or braids such as, without limitation, a 72 nitinol (NiTi) wire mesh strand braided configuration. In other embodiments, the occlusion device comprises wire mesh strands or braids that range from 36 to 144 NiTi strand braided configuration.

In another embodiment of an occlusion device disclosed herein, the 30 bolus of additional resilient mesh housed within the 20 body, comprises a relatively uniform distribution of wire mesh strands or braids such as, without limitation, a 72 nitinol (NiTi) wire mesh strand braided configuration. In other embodiments, the 30 bolus of the occlusion device comprises wire mesh strands or braids that range from 36 to 144 NiTi strand braided configuration. In one embodiment, the resilient mesh of the 20 body of the device is comprised of dissimilar metal(s) compared to the metal(s) within the additional resilient mesh of the 30 bolus within the 20 body.

In another embodiment, the mesh density of the inner 30 bolus is a double layer of mesh and is greater (or higher) than the mesh density of its 20 body's outer double layer of mesh.

An occlusion device disclosed herein is configured with resilient mesh material of a mesh density sufficient for functioning in such a manner as an endothelial cell scaffold within a vessel or across the 80 opening of the LAA and thereby reducing blood flow by about 60% to trigger clot formation and/or healing of the LAA. For the purposes of the present invention, the terminology "mesh density" means the level of porosity or the ratio of metal to open area of the mesh device. Mesh density relates to the number and size of the openings or pores of the mesh and by the extent that the pores are open or closed in situations where opening or pore openness varies between delivery and deployment. Generally, a high mesh density region of a resilient mesh material has approximately about 70% or more metal area and about 60% or less open area.

In one embodiment, the resilient mesh 20 body has an "open mesh density" for enhanced tissue integration and/or stabilization of the occlusion device. Open mesh density is greater than about 40% open area in the mesh. Open mesh density is known to have a low number, usually between about 40 and 80, picks per inch (PPI) to represent the porosity of the mesh layers. PPI is the number of repeat cross overs of braiding material in a linear inch. A high number of repeats (or PPI), usually between about 100 and 180, is an indicator that the mesh is dense. A lower number of repeats (or PPI) is an indicator that the mesh is porous (open). In an additional embodiment, the resilient mesh 20 body is constructed from a super elastic material, such as, without limitation, nitinol. In yet another embodiment, the resilient mesh 20 body is constructed from DFT platinum core nitinol. In other embodiments, when the 20 body mesh is constructed of nitinol, the 30 bolus within that 20 body mesh is constructed of DFT platinum core nitinol. In yet other embodiments, when the 20 body is constructed of DFT platinum core nitinol, the 30 bolus within that 20 body mesh is constructed of nitinol. DFT platinum core nitinol is used for enhancing visualization of the device during deployment and implantation.

FIGS. 1 and 2 also show the position of the 40 marker band, having a 90 proximal end and a 100 distal end, on an occlusion device of the present invention. The 40 marker is attached to the 20 body of the occlusion device and the body extends from the 100 distal end of the 40 marker band. In FIG. 2, the 90 proximal end of the 20 marker band is shown resting across, in the manner of a bridge, the 80 opening of the LAA to be treated, which, when combined with the properties of the low profile 14 resilient mesh 20 body comprising a 30 bolus of additional mesh, creates an open mesh density effect thereby promoting more effective endothelialization around the device. Other advantages include eliminating the need for incorporating additional mesh material extending proximally from the marker band in order to seal the 80 opening of the LAA or to anchor the device in the left atrial space. In addition, positioning the 90 proximal end of the 40 marker band to rest across the 80 opening of the LAA advantageously provides for full retrievability of the device.

In one embodiment of the device disclosed herein, a coil-wound core wire (or guide wire) of the catheter (or micro-catheter) is attached inside the 40 marker band at its 90 distal end to the ends of the 20 body of a dual layer of mesh. The coil wind maintains a constant diameter ($\phi$) so as not to impact upon flexibility or stiffness of the delivery catheter or micro-catheter or guide wire. In certain embodiments, FEP (Fluorinated Ethylene Propylene) heat shrink tubing encases the coil-wound portion of the core wire. Numerous readily available and well known attachment techniques in the medical device arts can be used to attach the distal end of the core wire inside the 40 marker band and/or to the occlusion device or implant. Such known techniques are also used to attach the ends of the resilient mesh 20 body to and/or inside/within the 40 marker band. Such attachment techniques include, without limitation, adhesives, laser melting, laser tack, spot, and/or continuous welding. In one embodiment, an adhesive is used to attach the distal end of the core wire inside the 40 marker band. In another embodiment, an adhesive is used to attach the ends of the resilient mesh 20 body to and/or inside/within the 40 marker band. In a further embodiment, the adhesive is an epoxy material which is cured or hardened through the application of heat or UV (ultra-violet) radiation. In an even further embodiment, the epoxy is a thermal cured, two-part epoxy such as EPO-TEK® 353ND-4 available from Epoxy Technology, Inc., 14 Fortune Drive, Billerica, Mass. In an additional embodiment, such an adhesive or epoxy material encapsulates the junction of the core wire inside the 40 marker band and increases its mechanical stability.

In another embodiment, during and/or after deployment of the device, the coil-wound core wire detaches the device disclosed herein at an electrolytic detachment site (or zone) on the core wire itself in such a manner so that the core wire is severed and/or dissolved through electrolytic action at the base of the 40 marker band. Such action then releases and/or places the occlusion device into an LAA to be treated.

In one embodiment, the 40 marker band of the occlusion device disclosed herein is a substantially solid collar or rigid member such as, without limitation a solid ring comprised of materials such as, without limitation, gold, platinum, stainless steel, and/or combinations thereof. In another embodiment, radiopaque materials such as, without limitation, gold, platinum, platinum/iridium alloy, and/or combinations thereof, can be used. Such a 40 marker provides visualization of the device during delivery and placement. The solidness of the 40 marker helps confer stability of the device within the LAA and prevents movement or the transfer of forces through the resilient mesh of the device thereby preventing misplacement or accidental movement of the device. The 40 marker is also configured with a junction (the core wire attachment inside the 40 marker band) to cooperate and release from/attach to a corresponding delivery means such as, without limitation, a delivery catheter or guide wire and/or pusher wire technologies. It also advantageously provides for full retrievability of the device disclosed herein.

In another embodiment, the substantially solid 40 marker band comprises a radiopaque material (such as for example, without limitation, platinum, gold, platinum/iridium alloy, and/or combinations thereof) to facilitate visualization of the occlusion device under fluoroscopy during delivery, placement and/or deployment. The 40 marker comprises a 90 proximal end and a 100 distal end. Each 20 arm of resilient mesh is attached to the 40 marker band and extends from the 100 distal end of the 40 marker band. In one embodiment, the 40 marker band may be configured to influence shape, diameter, and/or curvature of the resilient mesh 20 body upon expansion of the occlusion device. The 40 marker may be designed in various shapes to influence the overall profile of the occlusion device to ensure a proper fit of the expanded/deployed occlusion device within the LAA 50 pouch.

In some embodiments of the occlusion device disclosed herein, the 40 marker band is a rigid member such as a ring, collar (such as, e.g., a crushed or flattened collar), band, or suture (such as e.g., a polymeric suture). Such a "substantially solid" or "rigid member" functions as a pinch point for gathering the ends of the 20 body of the device. In a further embodiment, the 40 marker band is reinforced and therefore mesh of the device traverses the 40 marker band to provide a continuous profile on the inner surface from the LAA 80 opening to the LAA 50 pouch. Such a reinforced 40 marker band comprises materials including, without limitation, plastically deformable and shape-memory resilient mesh material, wire braided mesh material (including various mesh braiding configurations such as, without limitation, 2 strands over—1 strand under, 1 strand under—1 strand over, 1 strand over—2 strands under, etc.), laser cut mesh material, and/or a combination thereof.

The substantially solid 40 marker band facilities delivery and positioning of the occlusion device adjacent the 80 opening of LAA by providing a rigid member to maneuver into the neck. Additionally, in some embodiments, the substantially solid 40 marker band provides visibility under fluoroscopy, thereby allowing more accurate visualization and exacting placement of the device.

In certain embodiments, the resilient mesh of the occlusion device disclosed herein can be filled with an embolic material such as, without limitation, liquid agents and/or particulates to promote clotting and closure of the LAA. Examples of liquid agents and particulates include, without limitation, gelatin foam, polyvinyl alcohol particles, trisacryl gelatin microspheres, N-butyl-2-cynoacrylate, ethylene vinyl alcohol copolymer, calcium alginate gel, absolute alcohol, and the like.

In other embodiments, the occlusion device disclosed herein may further incorporate and/or be used with adjunctive elements and/or members well known in the art such as coiling techniques, framing coils, embolic agents, additional markers, polymers, resorbent polymers and/or a combination thereof.

Resilient mesh materials for design and/or manufacture of occlusion devices are readily available and well known by those skilled in the relevant art. As such, resilient mesh materials range from a wide variety of available materials such as, without limitation, nickel titanium (nitinol or otherwise known as NiTi), stainless steel, polymers, and/or combinations thereof. Exemplary known biomedical polymeric families include, without limitation, polymers such as polyphosphazenes, polyanhydrides, polyacetals, poly(ortho esters), polyphosphoesters, polycaprolactones, polyurethanes, polylactides, polycarbonates, polyamides, and/or a combination thereof. (See, e.g., J Polym Sci B Polym Phys. Author manuscript; available in PMC 2012 June 15.)

In one exemplary embodiment, the resilient mesh material is formed of woven strands of polymer material, such as, without limitation, nylon, polypropylene or polyester. The polymer strands can be filled with a radiopaque material which allows the physician treating the aneurysm to fluoroscopically visualize the location of the device within the vasculature. Radiopaque filler materials preferably include bismuth trioxide, tungsten, titanium dioxide or barium sulfate, or radiopaque dyes such as iodine. The resilient mesh material can be formed by strands of radiopaque material. The radiopaque strands allow the physician and/or radiologist to fluoroscopically visualize the location of the mesh, without the use of filled polymer materials. Such radiopaque strands may be formed with materials such as, without limitation, gold, platinum, a platinum/iridium alloy, and/or a combination thereof. In one embodiment, the resilient mesh material is constructed of 10%-20% platinum core NiTi. In another embodiment, the resilient mesh material is constructed of 10% platinum core NiTi, 15% platinum core NiTi, or 20% platinum core NiTi. 10% platinum core NiTi construction is sufficient to provide a ghost image of the occlusion device under x-ray.

Such constructed combination wires or composite wires having a radiopaque core and non-radiopaque outer layer or casing are readily available and well known in the medical device and metallic arts as DFT® (drawn-filled-tube) wires, cables or ribbons. DFT® wire is a metal-to-metal composite constructed to combine the desired physical and mechanical attributes of two or more materials into a single wire. By placing the more radiopaque, but more ductile material in the core of the wire, the NiTi outer layer is able to provide the resulting composite wire with similar mechanical properties of a 100% NiTi wire. DFT® wires are available from Fort Wayne Metals Corp., Fort Wayne, Ind., U.S.A. See also, for example, the journal article entitled Biocompatible Wire by Schaffer in Advanced Materials & Processes, Oct. 2002, pages 51-54, incorporated herein by reference.

Where the resilient mesh material is formed of radiopaque metal strands, the strands may be covered with a polymer coating or extrusion. The coating or extrusion over the radiopaque wire strands provides fluoroscopic visualization but also increases the resistance of the strands to bending fatigue and may also increase lubricity of the strands. The polymer coating or extrusion, in one embodiment, is coated or treated with an agent which tends to resist clotting, such as heparin. Such clot resistant coatings are generally known. The polymer coating or extrusion can be any suitable extrudable polymer, or any polymer that can be applied in a thin coating, such as Teflon® or polyurethane.

In yet another embodiment, the strands of the resilient mesh material are formed using both metal and polymer braided strands. Combining the metal strands with the polymer strands into a braid changes the flexibility characteristics of mesh. The force required to deploy and/or collapse such a mesh portion is significantly reduced over that required for a mesh portion that includes only metal mesh strands. However, the radiopaque characteristics of the mesh for fluoroscopic visualization are retained. Metal strands forming such a device includes, without limitation, stainless steel, gold, platinum, platinum/iridium, nitinol, and/or combinations thereof. Polymer strands forming the device can include nylon, polypropylene, polyester, Teflon®, and/or combinations thereof. Further, polymer strands of the mesh material can be chemically modified to make them radiopaque with known techniques such as, without limitation, by using gold deposition onto the polymer strands, or by using ion beam plasma deposition of suitable metal ions onto the polymer strands.

The resilient mesh material can also be formed with filaments or strands of varying diameter and/or varying flexibility. By varying the size or flexibility of the polymer strands, the flexibility characteristics of the mesh, upon deployment, can also be varied. By varying the flexibility characteristics, both the deployed and collapsed configuration of the resilient mesh 20 body can be varied or changed to substantially any desired shape.

Not only can the mesh be formed of both polymer strands or filaments and metal strands or filaments, but it can also be formed using filaments of different polymer materials. For example, different polymer materials having different flexibility characteristics can be used in forming the mesh. This alters the flexibility characteristics of the device to change the resultant configuration of the mesh 20 body in both the deployed and the collapsed positions. Such biomedical polymers are readily known and available in the art and can be derived from polymeric families such as, without limitation, polyphosphazenes, polyanhydrides, polyacetals, poly (ortho esters), polyphosphoesters, polycaprolactones, polyurethanes, polylactides, polycarbonates, polyamides, and/or a combination thereof.

Resilient mesh materials suitable for use within the device may take the form of a flat woven sheet, knitted sheet, or a laser cut wire mesh. In general, the material should include two or more sets of substantially parallel strands, with one set of parallel strands being at a pitch of between 45 degrees and 135 degrees with respect to the other set of parallel strands. In some embodiments, the two sets of parallel strands forming the mesh material are substantially perpendicular to each other. The pitch and general construction of the mesh material may be optimized to meet the performance needs of the occlusion device.

The wire strands of the metal fabric used in the present invention should be formed of a material which is both resilient and can be heat-treated to substantially set a desired shape. Materials which are believed to be suitable for this purpose include a cobalt-based low thermal expansion alloy referred to in the field of occlusion devices as Elgiloy® (available from Eligiloy Specialty Metals, Elgin, Illinois), nickel-based high-temperature high-strength "superalloys" commercially available from Haynes International under the trade name Hastelloy®, nickel-based heat treatable alloys sold under the name Incoloy® by International Nickel, and a number of different grades of stainless steel. The important factor in choosing a suitable material for the wires is that the wires retain a suitable amount of the deformation induced by the molding surface (or shape memory, as described below) when subjected to a predetermined heat treatment.

One class of materials which meet these qualifications are so-called shape memory alloys. Such alloys tend to have a temperature induced phase change which will cause the material to have a preferred configuration which can be fixed by heating the material above a certain transition temperature to induce a change in the phase of the material. When the alloy is cooled, the alloy will "remember" the shape it was in during the heat treatment and will tend to assume that same and/or similar configuration unless constrained from doing so.

One particular shape memory alloy for use in the present invention is nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here. For example, U.S. Pat. Nos. 5,067,489 and 4,991, 602, the teachings of which are incorporated herein by reference, discuss the use of shape memory NiTi alloys in guide wire-based technologies. Such NiTi alloys are preferred, at least in part, because they are commercially available and more is known about handling such alloys than other known shape memory alloys. NiTi alloys are also very elastic. Indeed, they are said to be known as "superelastic" or "pseudoelastic." This elasticity will help an occlusion device as disclosed herein to return to prior expanded configuration for deployment thereof.

The wire strands can comprise a standard monofilament of the selected material, i.e., a standard wire stock may be used. In some embodiments, 72 wire strands and/or 72 strand braid configuration may be used. In other embodiments, the occlusion device comprises wire mesh strands or braids that range from 36 to 144 NiTi strand braided configurations. If so desired, though, the individual wire strands may be formed from "cables" made up of a plurality of individual wires. For example, cables formed of metal wires where several wires are helically wrapped about a central wire are commercially available and NiTi cables having an outer diameter of 0.003 inches or less can be purchased. One advantage of certain cables is that they tend to be "softer" than the monofilament wires having the same diameter and formed of same material. Additionally, the use of a cable can increase the effective surface area of the wire strand, which will tend to promote thrombosis.

In some embodiments, the resilient mesh may be formed uniformly of the same material; however such material may have different knitted, stitched, braided, and/or cut construction.

In other embodiments, the occlusion device disclosed herein can be used, when scaled accordingly, in endovascular techniques such as for the treatment and/or amelioration of aneurysms, particularly large and irregular sized aneurysms, and to promote more effective endothelialization around the device. In this regard, reference is made to commonly owned, U.S. patent application Ser. No. 14/699,188; which is incorporated herein by reference. Additionally, the occlusion device disclosed herein can be used, when scaled accordingly, in the process of peripheral vascular embolization (a process well known in the art and known to involve the shutdown of blood flow distal to a specified vascular point), for example, in the treatment and/or amelioration of peripheral arterial or venous pathologies and/or any related pathologies requiring vessel occlusion for the treatment thereof.

The occlusion device of the present invention may incorporate reasonable design parameters, features, modifications, advantages, and variations that are readily apparent to those skilled in the art in the field of occlusion devices.

What is claimed is:

1. An occlusion device comprising:
   (a) a substantially solid marker band having an inner and outer diameter, a proximal end, and a distal end; and
   (b) a resilient mesh body attached within the substantially solid marker band,
   wherein the resilient mesh body has a length y,
   wherein the occlusion device comprises a bolus of additional resilient mesh material of a length x arranged within the resilient mesh body, wherein y is greater than x,
   wherein the resilient mesh body extends distally from the substantially solid marker band,
   wherein the resilient mesh body has a first delivery shape and a second expandable deployed shape, and
   wherein the second expandable deployed shape is in a shape of an inverted mushroom.

2. The occlusion device according to claim 1, wherein the resilient mesh body has a first predetermined mesh density and the bolus of additional resilient mesh material has a second predetermined mesh density.

3. The occlusion device according to claim 2, wherein the second predetermined mesh density is higher than the first predetermined mesh density.

4. The occlusion device according to claim 3, wherein the bolus of additional resilient mesh material is an inner double layer of mesh and the resilient mesh body is an outer double layer of mesh.

5. The occlusion device according to claim 4, wherein the resilient mesh body and the bolus of additional resilient mesh material are made of dissimilar metals.

6. The occlusion device according to claim 4, wherein the resilient mesh body is formed of a polymer material.

7. The occlusion device according to claim 6, wherein the bolus of additional resilient mesh material is formed of a polymer.

8. The occlusion device according to claim 7, wherein the resilient mesh body and the bolus of additional resilient mesh material are formed of the same polymer material.

9. The occlusion device according to claim 1 wherein the resilient mesh body is formed of nitinol.

10. The occlusion device according to claim 9, wherein the bolus of additional resilient mesh material is formed of nitinol.

11. The occlusion device according to claim 10, wherein the nitinol comprises from 36 to 144 NiTi strand braided configuration.

12. The occlusion device according to claim 1, wherein the resilient mesh body is constructed from DFT platinum core nitinol.

13. The occlusion device of claim 1, wherein the resilient mesh body is configured to be deployed in a Left Atrial Appendage (LAA).

14. The occlusion device of claim 1, wherein the resilient mesh body has an open mesh density.

15. The occlusion device according to claim 14, wherein the open mesh density is between 40 picks per inch and 80 picks per inch.

16. A method of treating an aneurysm or a left atrial appendage, comprising:
   delivering an occlusion device to an aneurysm or a left atrial appendage, wherein the occlusion device comprises:
   (a) a substantially solid marker band having an inner and outer diameter, a proximal end, and a distal end,
   (b) a resilient mesh body attached within the substantially solid marker band, and
   (c) a bolus of additional resilient mesh material of a length x arranged within the resilient mesh body,
   wherein the resilient mesh body has a length y,
   wherein y is greater than x and wherein the resilient mesh body extends distally from the substantially solid marker band,
   wherein the resilient mesh body has a first delivery shape and a second expandable deployed shape, and
   wherein the second expandable deployed shape is in a shape of an inverted mushroom; and
   deploying the occlusion device in the aneurysm or the left atrial appendage.

17. The method of claim 16, wherein the resilient mesh body has a first predetermined mesh density and the bolus of additional resilient mesh material has a second predetermined mesh density, and wherein the second predetermined mesh density is higher than the first predetermined mesh density.

18. The method of claim 16, wherein the bolus of additional resilient mesh material is an inner double layer of mesh and the resilient mesh body is an outer double layer of mesh.

19. The method of claim 16, wherein the resilient mesh body and the bolus of additional resilient mesh material are made of dissimilar metals.

20. The method of claim 16, wherein the resilient mesh body has an open mesh density, and wherein the open mesh density is between 40 picks per inch and 80 picks per inch.

* * * * *